(12) United States Patent
Swenson et al.

(10) Patent No.: US 8,226,576 B2
(45) Date of Patent: Jul. 24, 2012

(54) SAFETY BLOOD COLLECTION HOLDER

(75) Inventors: Kirk D. Swenson, North Caldwell, NJ (US); James C. Schneider, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1317 days.

(21) Appl. No.: 10/786,725

(22) Filed: Feb. 25, 2004

(65) Prior Publication Data
US 2005/0187493 A1     Aug. 25, 2005

(51) Int. Cl.
*A61B 5/00*     (2006.01)
*B65D 81/00*    (2006.01)

(52) U.S. Cl. ........ 600/576; 600/573; 600/578; 604/198; 604/240; 604/263

(58) Field of Classification Search .................. 600/576; 604/187, 192, 198, 263, 240–243
See application file for complete search history.

(56) References Cited

U.S. PATENT DOCUMENTS

| | | | |
|---|---|---|---|
| 2,806,473 A * | 9/1957 | Lingley ................. | 604/243 |
| 4,822,343 A * | 4/1989 | Beiser .................. | 604/187 |
| 4,982,842 A * | 1/1991 | Hollister .............. | 206/365 |
| 4,994,046 A * | 2/1991 | Wesson et al. ........ | 604/198 |
| 5,055,102 A * | 10/1991 | Sitnik ................. | 604/192 |
| 5,102,397 A * | 4/1992 | Brunet ................. | 604/192 |
| 5,139,489 A | 8/1992 | Hollister | |
| 5,154,285 A | 10/1992 | Hollister | |
| 5,188,611 A | 2/1993 | Orgain | |
| 5,197,954 A * | 3/1993 | Cameron .............. | 604/110 |
| 5,201,716 A * | 4/1993 | Richard ............... | 604/187 |
| 5,207,653 A * | 5/1993 | Janjua et al. ........ | 604/192 |
| 5,277,311 A * | 1/1994 | Hollister ............. | 206/365 |
| 5,445,619 A | 8/1995 | Burns | |
| 5,490,841 A * | 2/1996 | Landis ................. | 604/110 |
| 5,643,219 A * | 7/1997 | Burns .................. | 604/192 |
| 5,662,617 A * | 9/1997 | Odell et al. .......... | 604/192 |
| 5,665,075 A | 9/1997 | Gyure et al. | |
| 5,681,295 A * | 10/1997 | Gyure et al. ......... | 604/263 |
| 5,886,249 A * | 3/1999 | Bonne et al. ........ | 73/24.02 |
| 6,059,737 A * | 5/2000 | Crawford ............ | 600/576 |
| 6,077,253 A * | 6/2000 | Cosme ................ | 604/263 |
| 6,139,533 A * | 10/2000 | Xia et al. ............ | 604/192 |
| 6,298,541 B1 | 10/2001 | Newby et al. | |
| 6,413,243 B1 | 7/2002 | Geist | |
| 6,436,086 B1 | 8/2002 | Newby et al. | |
| 6,440,104 B1 | 8/2002 | Newby et al. | |
| 6,695,819 B2 * | 2/2004 | Kobayashi ........... | 604/192 |
| 6,719,737 B2 * | 4/2004 | Kobayashi ........... | 604/263 |
| 6,824,531 B1 | 11/2004 | Zecha, Jr. et al. | |
| 2003/0028152 A1 | 2/2003 | Alesi et al. | |
| 2003/0093009 A1 | 5/2003 | Newby et al. | |
| 2003/0181861 A1 | 9/2003 | Wilkinson | |

FOREIGN PATENT DOCUMENTS

EP    1 371 383 A1    12/2003

* cited by examiner

*Primary Examiner* — Rene Towa
(74) *Attorney, Agent, or Firm* — The Webb Law Firm

(57) ABSTRACT

The present invention is a holder assembly having a holder housing, collar and safety shield. The safety shield is pivotably attached to the collar. The collar is receiving within a recess defined by the annular skirt and needle receiving port of the holder housing. The collar and attached safety shield may thus be rotated about the holder housing and an attached needle assembly, thereby allowing a user to freely position the safety shield during needle insertion and preventing the dislocation of safety shield from the holder housing.

9 Claims, 12 Drawing Sheets

SAFETY BLOOD COLLECTION HOLDER

BACKGROUND OF THE INVENTION

1. Field of the Invention

The present invention relates to a safety needle holder assembly having a safety shield which is rotatable about the holder housing.

2. Description of Related Art

Needle holders, in conjunction with an evacuated collection tube and needle cannula, are routinely used by doctors, phlebotomists, nurses and the like to draw body fluid samples from a patient. During the use of such a collection needle assembly, the distal end of the needle cannula in the needle holder is inserted into a vein of the patient. The evacuated collection tube is then inserted into the rearward end of the needle holder until a needle (the proximal end of a double-ended needle cannula) within the needle holder pierces a closure on the end of the tube. The vacuum in the tube then draws a body fluid sample from the patient through the needle cannula and into the tube. After the collection process is complete the needle cannula is removed from the vein and disposed of.

Because of the great concern that users of such needles may be contaminated with the blood of a patient by accidental sticks from the contaminated needle, it is preferable to cover the contaminated needle as soon as it is removed from the vein. For this reason, many developments have been made to provide means for covering the contaminated needle, once it is removed from the patient. These devices usually involve some sort of shield arrangement that moves in place over the contaminated needle once it has been removed from the patient. However, these shield arrangements typically require the use of one or two hands to perform the operation of moving the shield over the contaminated needle, which is a hindrance to the user. In addition, it is also difficult to position the safety shield in a location where it does not interfere with the action of inserting the needle into the patient's vein.

A number of devices incorporate a safety shield assembly in which the shield can be pivoted away from the needle during use and pivoted about the needle after use for protection from the used needle. U.S. Pat. No. 5,188,611 discloses a reusable safety needle arrangement having a collar for engaging a needle and a slotted longitudinal shield which is attached to the collar at a hinge for pivoting over the needle. The arrangement includes a locking mechanism for locking the shield over the needle, which locking mechanism is provided through a set of flanges on the shield which grip a set of complementary catches on the collar. U.S. Pat. Nos. 6,298,541 and 6,440,104 disclose a safety shield assembly for a double-ended needle for blood collection procedures with a safety shield attached to the needle hub through a collar. The hub includes threads for engaging a conventional needle holder such as that used with the VACUTAINER™ brand of blood collection assemblies sold by Becton, Dickinson and Company. While such shielding assemblies are effective, the safety shield cannot be rotated out of the way during needle insertion.

U.S. Pat. No. 5,154,285 discloses a safety shield which attaches to the external surface of the holder housing. Specifically, the holder housing has a circumferential protuberance on the outer circumference of the needle port. The base of the safety shield has a corresponding internal circumferential groove which mates with the holder housing protuberance. The shield thus attaches to the outer circumference of the holder housing. Although the base of the shield is rotatable around the exterior of the holder housing, this design does not provide a mechanism which prevents the shield from becoming disconnected from the holder during use.

Thus, there remains a need for a safety holder assembly wherein the safety shield is attached collar rotates within the holder housing, thus preventing the safety shield from becoming disconnected therefrom during use.

SUMMARY OF THE INVENTION

The present invention is directed to a safety needle holder assembly and a method for assembling the assembly. The assembly allows for the rotation of the pivotable safety shield about the holder, wherein the safety shield is connected to a collar which rotates within a skirt extending from the forward end of the holder housing.

The assembly of the present invention preferably comprises a safety shield pivotably connected to a collar and a holder housing. One skilled in the art will understand that the assembly of the present invention is intended to be used in conjunction with a needle and hub assembly as described in U.S. Pat. Nos. 6,440,104 and 6,298,541, which are incorporated herein by reference thereto.

Preferably, the safety shield comprises a rearward end, a forward end, a slot or longitudinal opening for housing a used needle in the forward end, means for securing the needle in the slot, means for guiding the needle into the slot, means for connecting the shield and the fluid handling device, means for guiding the user's fingers to move the shield into various positions, and means for retaining the shield securely over the used needle.

Desirably, the safety shield is connected to the assembly by the collar. Preferably, the shield is movably connected to the collar which is connected to the holder housing. Preferably, the safety shield is connected to the collar by a hanger bar that engages with a hook arm that is located on the collar so that the safety shield may be pivoted with respect to the collar and the safety shield is able to easily move into several positions. It is within the purview of the present invention to include any structure for connecting the shield to the collar so that the shield may be pivoted with respect to the collar. These structures include known mechanical hinges and various linkages, living hinges, or combinations of hinges and linkages.

Most preferably, the safety shield is connected to the collar by interference fit between the hanger bar and the hook bar. Therefore, the safety shield is always oriented in a stable position and will not move forward or backwards unless movement of the safety shield relative to the hanger bar and the hook bar is positively initiated by the user.

Alternatively, it is within the purview of the present invention that the shield and collar is a unitary one-piece structure. The one-piece structure may be accomplished by many methods including molding the safety shield and the collar as a one-piece unit.

The collar includes a protrusion on its outer circumference. Preferably, the protrusion is a circumferential annular protrusion. The forward end of the holder housing includes a needle receiving port, and spaced outwardly therefrom, an annular skirt. The annular skirt and needle receiving port define a recess therebetween, which extends around the outer circumference of the needle receiving port. The inner surface of the annular skirt preferably defines a groove which is adapted to receive the protrusion of the collar. The collar is thus received in the recess defined between the annular skirt and the needle receiving port of the holder housing. The collar and the safety shield are rotatable about the centerline axis of the holder housing (and thus the needle) within the annular skirt of the holder housing.

With proper molding, the friction between the protrusion of the collar and the groove of the holder housing's annular skirt can be made so that force must be applied to rotate the collar and safety shield. The shield thus can be set in various positions of angularity during venipuncture.

The annular skirt of the holder housing may also be constructed so that it extends from the holder housing to a position which abuts or encloses the open end of the hook arm. This abutment or enclosure prevents the interface fit between the hanger bar/hook arm attachment of the safety shield and collar from releasing.

Desirably, the assembly of the present invention may be used with a syringe assembly, a hypodermic needle, a needle assembly, a needle assembly with a needle holder, a blood collection set, an intravenous infusion set or other fluid handling devices. Preferably, the assembly of the present invention is used with a needle assembly comprising a needle and a hub. Preferably, the needle is a conventional double-ended needle.

Most preferably, the present invention is used with a needle assembly comprising a hub and a needle connected to the hub whereby the needle comprises a non-patient end and an intravenous end. The collar of the present invention fits around the hub. The hub threads into the needle receiving port of the holder housing.

BRIEF DESCRIPTION OF THE DRAWING(S)

DESCRIPTION OF THE PREFERRED EMBODIMENT(S)

Figure 1:
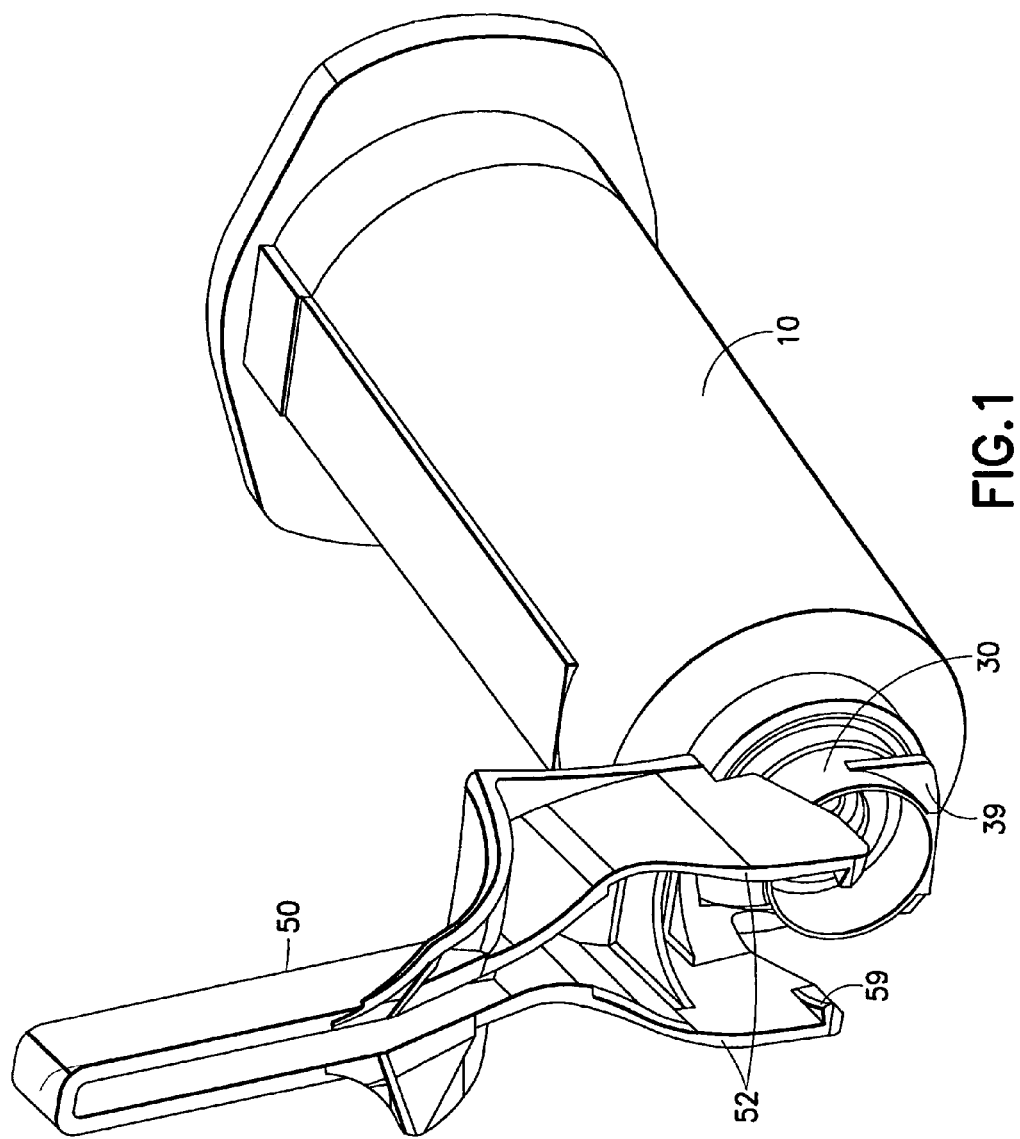
FIG. 1 is a perspective view of the assembly of the present invention.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
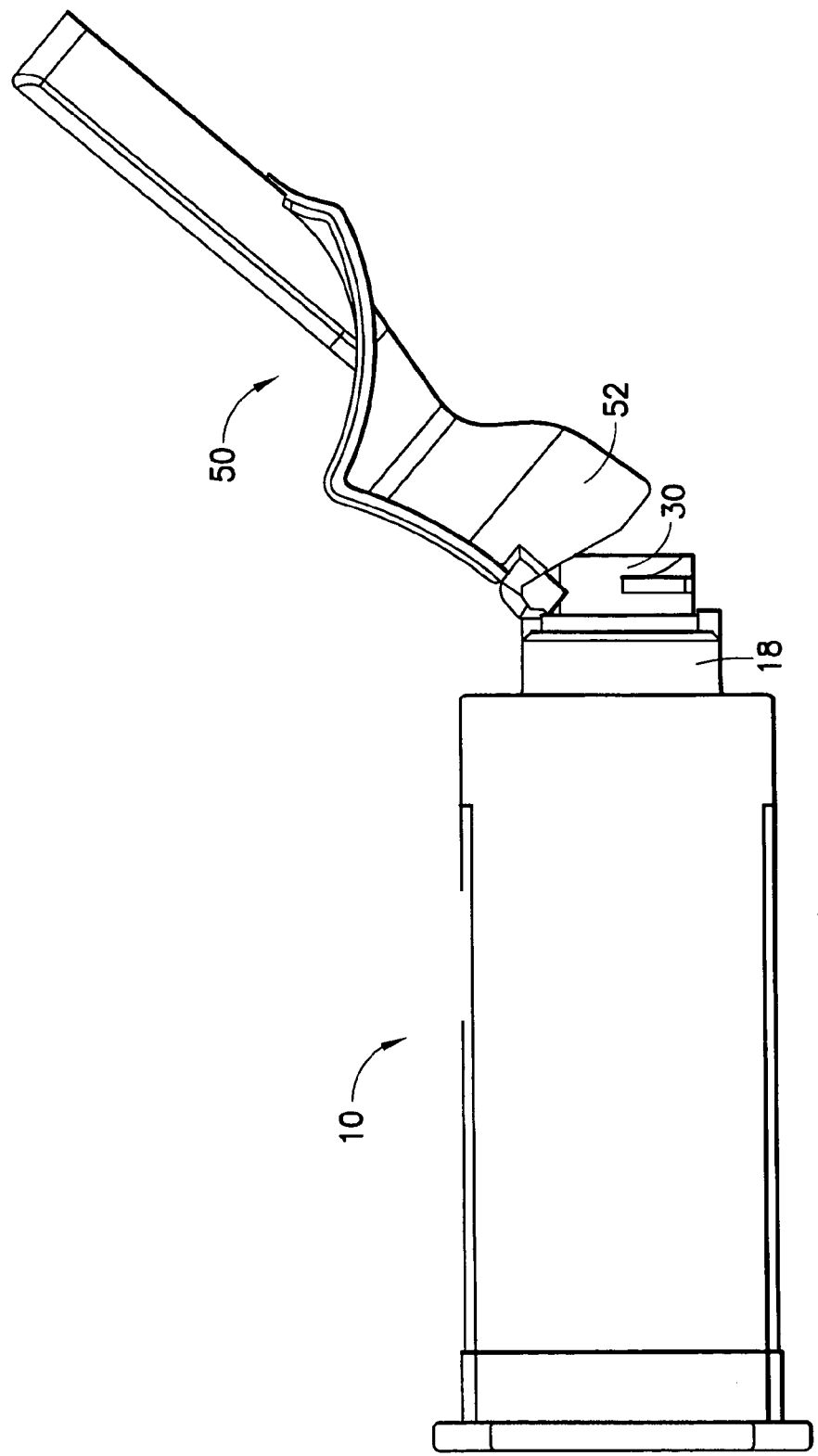
FIG. 2 is a side view of the assembly of FIG. 1.
Figure 3:
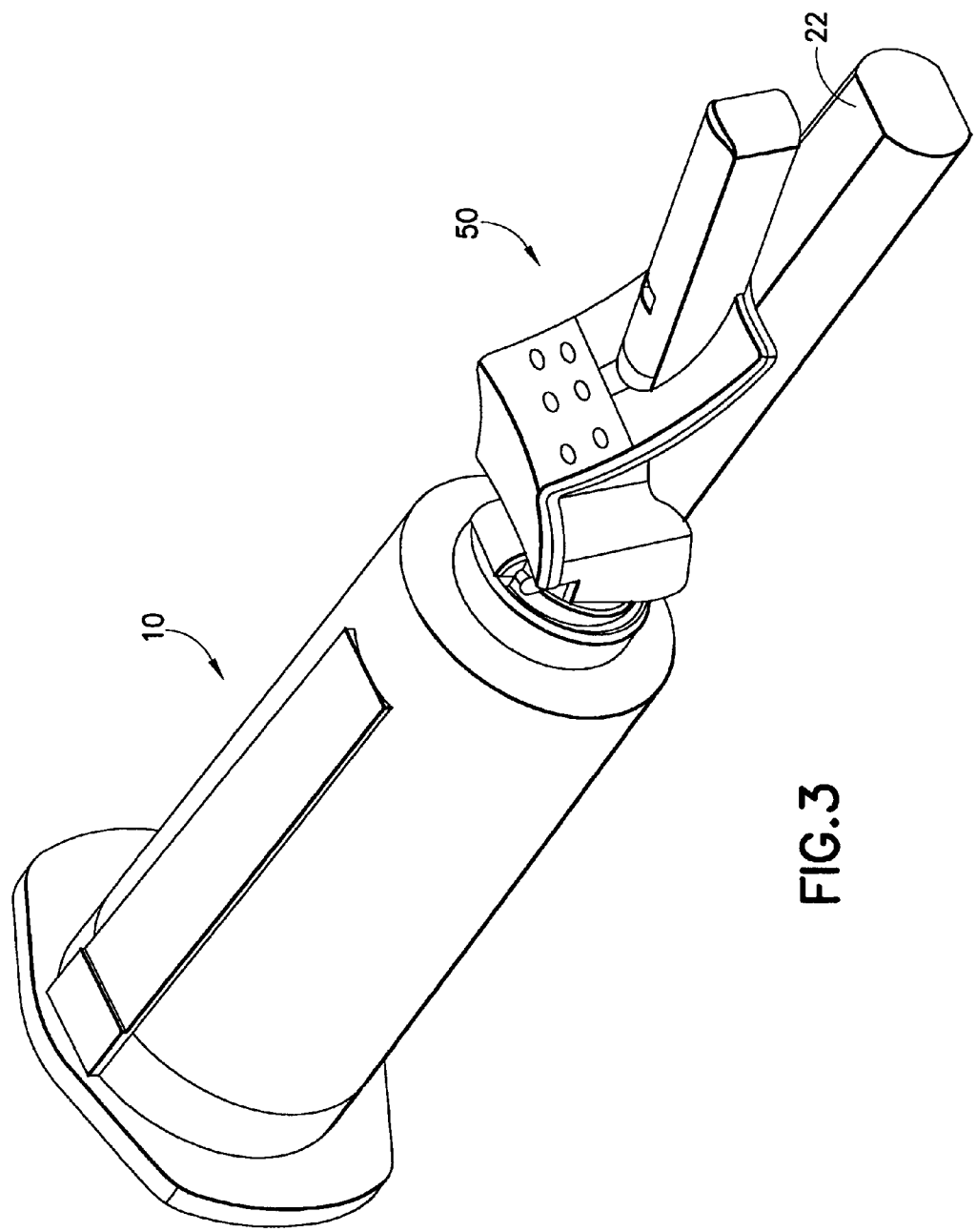
FIG. 3 is a perspective view of the assembly of the present invention shown connected to a needle assembly.
Figure 4:
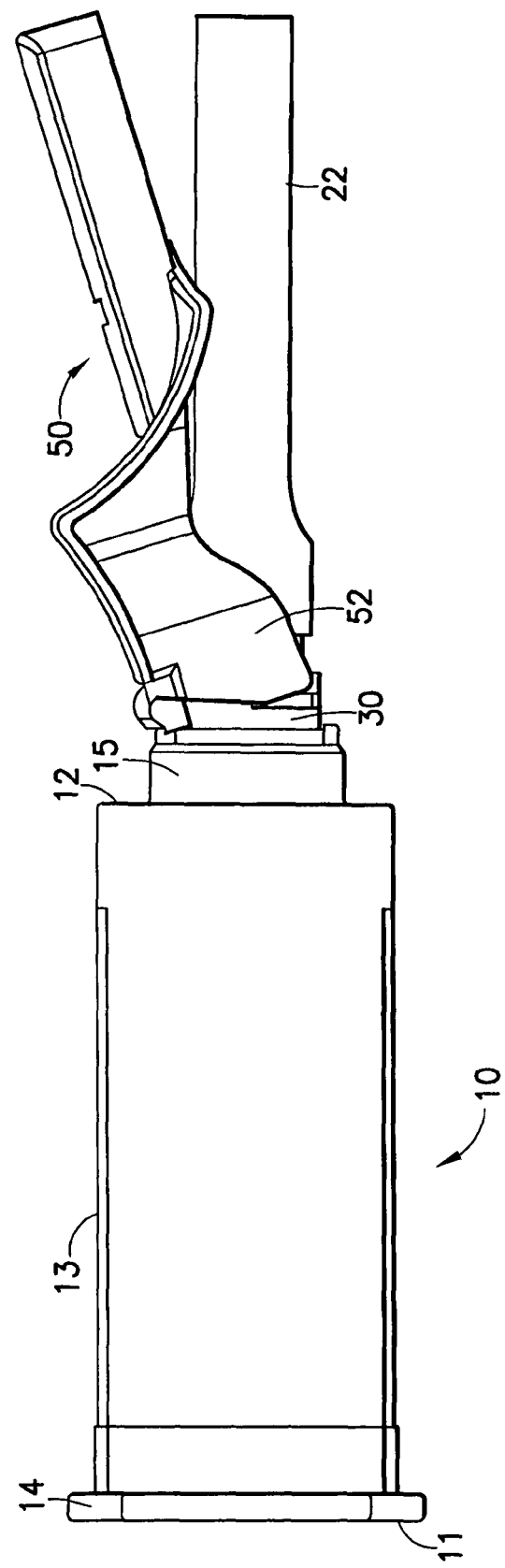
FIG. 4 is a side view of the assembly of FIG. 3.

Referring to the drawings in which like reference characters refer to like parts throughout the several views thereof, FIGS. 1 and 2 illustrate a holder assembly according to the present invention, and FIGS. 3-6 illustrate the holder assembly attached to a needle assembly through hub, with a packaging cover over the needle. The holder assembly generally includes a holder housing 10, collar 30 and safety shield 50. The needle assembly includes a needle 20 and hub 21. In its packaged condition, the needle is covered by rigid sleeve 22 acting as a packaging cover.

Figure 8:
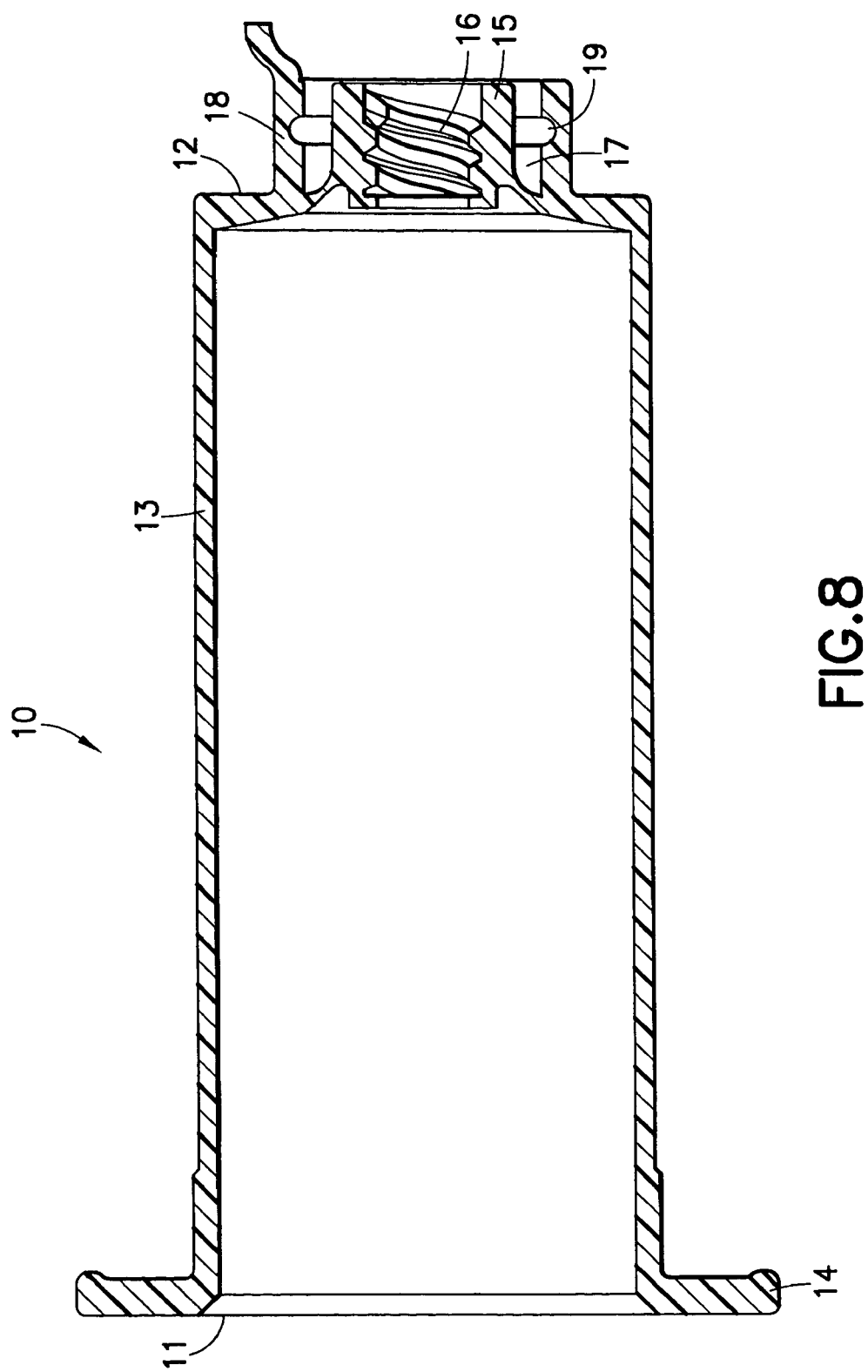
FIG. 8 is a cross-section view of the holder housing.

FIGS. 1 and 2 depict the holder assembly in a preferred embodiment, including safety shield 50 attached to the front end of holder housing 10 through collar 30. Referring to FIG. 8, holder housing 10 includes a generally tubular body extending between a rearward end 11 and a forward end 12, and defined by tubular wall 13. Rearward end 11 of holder housing 10 is widely open and is adapted to receive a blood collection tube (not shown). However, rearward end 11 of holder housing 10 may have a removable seal or cap (not shown) for maintaining sterility during storage. Rearward end 11 of holder housing 10 also includes a radially aligned flange 14 to facilitate manipulation of holder housing 10 during use. Flange 14 is desirably non-circular to prevent holder housing 10 from rolling. Flange 14 desirably includes a linear edge extending along a bottom surface of holder housing 10 to provide a clear indication of the top and bottom sides of holder housing 10. Forward end 12 of holder housing 10 is adapted for mating with a needle assembly, as discussed in more detail herein.

Holder housing 10 further includes recess 17 which is internally defined by needle receiving port 15 and externally defined by skirt 18. Skirt 18 is preferably annular in shape and may be referred to herein as "annular skirt 18". Annular skirt 18 preferably extends around the entire circumference of needle receiving port 15, thus defining recess 17 which extends circumferentially around needle receiving port 15. Recess 17 desirably includes groove 19, which is defined within the interior side of annular skirt 18. Groove 19 is preferably annular in shape and extends within the entire circumference of the interior side of annular skirt 18. Forward end 12 of holder housing 10 is adapted to receive a separate needle assembly therethrough, and therefore may include structure for mating with such a separate needle assembly, such as needle receiving port 15 which may be formed with internal threads 16, as will be discussed in more detail herein.

Figure 9:
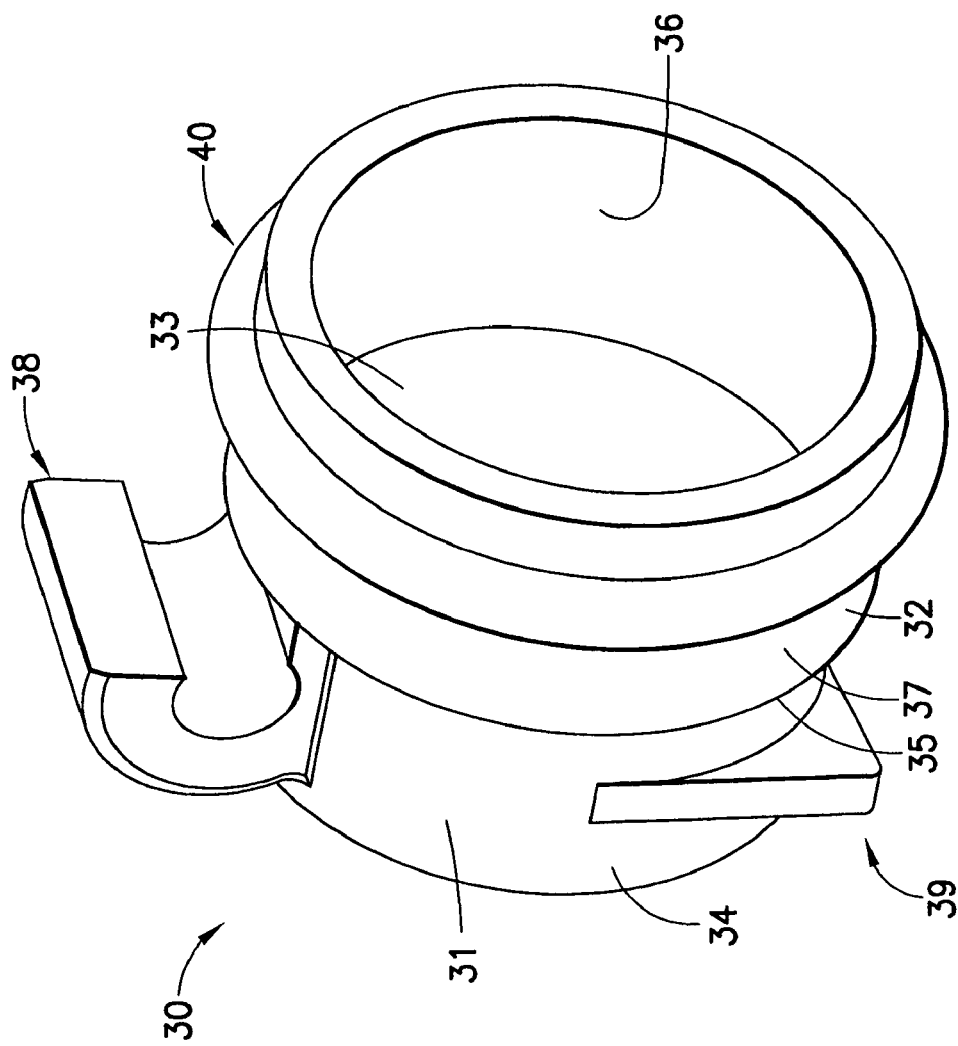
FIG. 9 is an enlarged perspective view of the collar of the assembly of the present invention.

As depicted in FIGS. 1-2, holder housing 10 is connected with pivotable safety shield 50 through collar 30. As shown in FIG. 9, collar 30 includes two sections, a forward collar section 31 and a rearward collar section 32. The collar is preferably annular in shape. The forward collar section 31 is cylindrical comprising an inner sidewall 33 and an outer sidewall 34, and mates with the rearward collar section at a shoulder 35. Rearward collar section 32 is cylindrical comprising an inner sidewall 36 and an outer sidewall 37 and extends from shoulder 35 opposite of forward collar section 31. The inner diameter of forward collar section 31 is larger than the inner diameter of rearward collar section 32. Alternatively, the inner diameters for collar 30 can be formed as a constant inner diameter of the same dimension.

Extending on outer sidewall 34 of forward collar section 31 is a hook member 38 and located opposite or downwardly of hook member 38 on outer sidewall 34 are hub locks or protrusions 39. Rearward collar section 32 includes protrusion 40. Protrusion 40 is preferably annular and extends circumferentially around outer sidewall 37.

Figure 7:
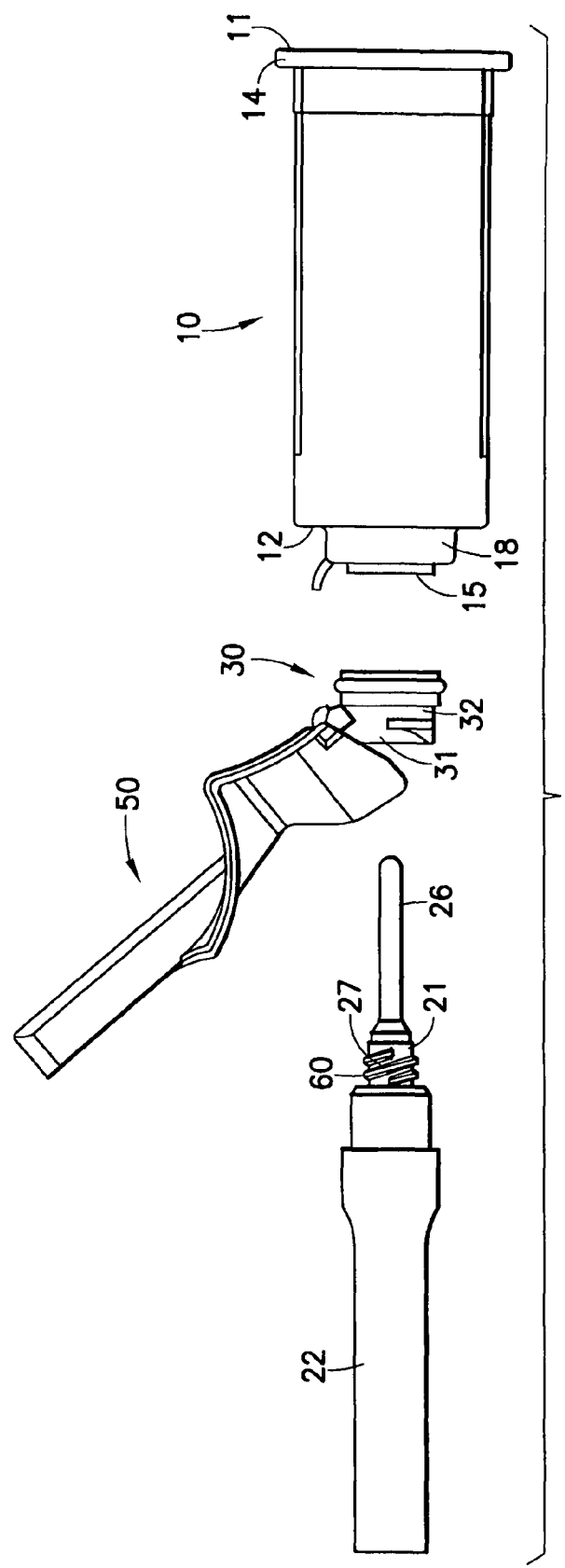
FIG. 7 is a side view of the unassembled pieces of FIG. 3.

FIGS. 1, 2 and 7 illustrate the pivotable safety shield 50. This structure is similar to the type described in U.S. Pat. No. 6,440,104, which is incorporated herein by reference. Safety shield 50 is preferably connected to the collar 30 through an interengaging structure for providing pivotable attachment.

For example, collar 30 may include hook member 38 extending from the outer sidewall 34, of forward collar section 31 of the collar 30. Hook member 38 pivotably engages with hanger bar 51 of pivot shield 50 providing a pivot hinge for the pivoting of safety shield 50 with respect to collar 30 about a pivot axis.

Figure 5:
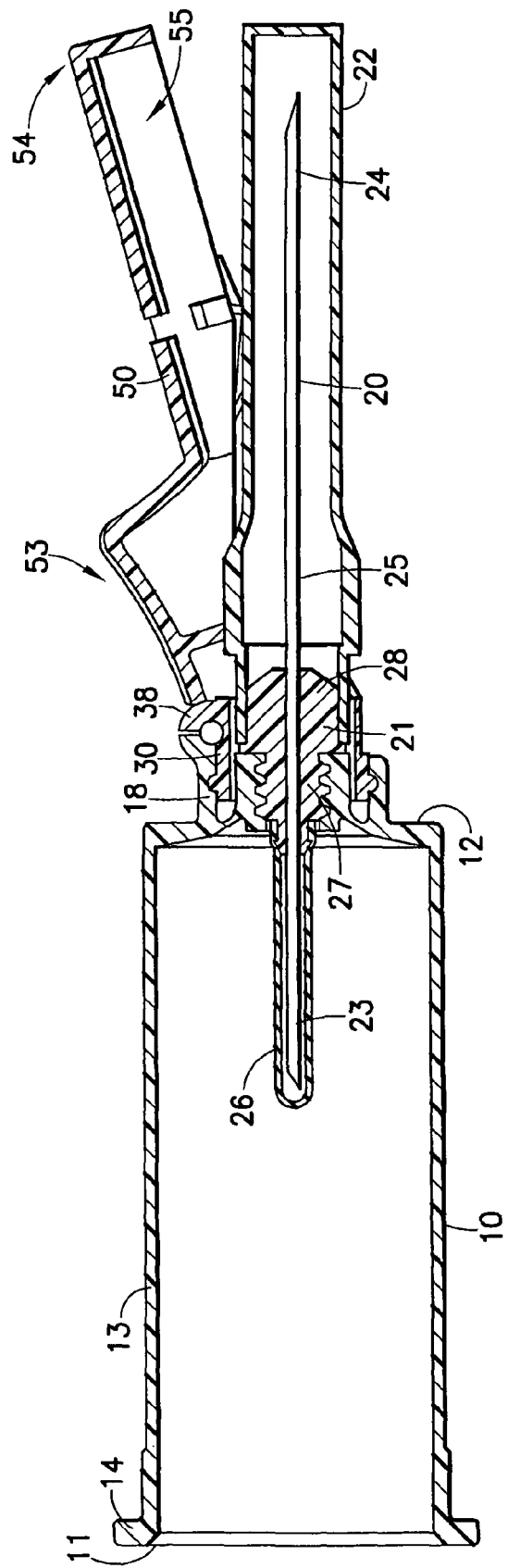
FIG. 5 is a cross-section view of the assembly FIG. 3.
Figure 10:
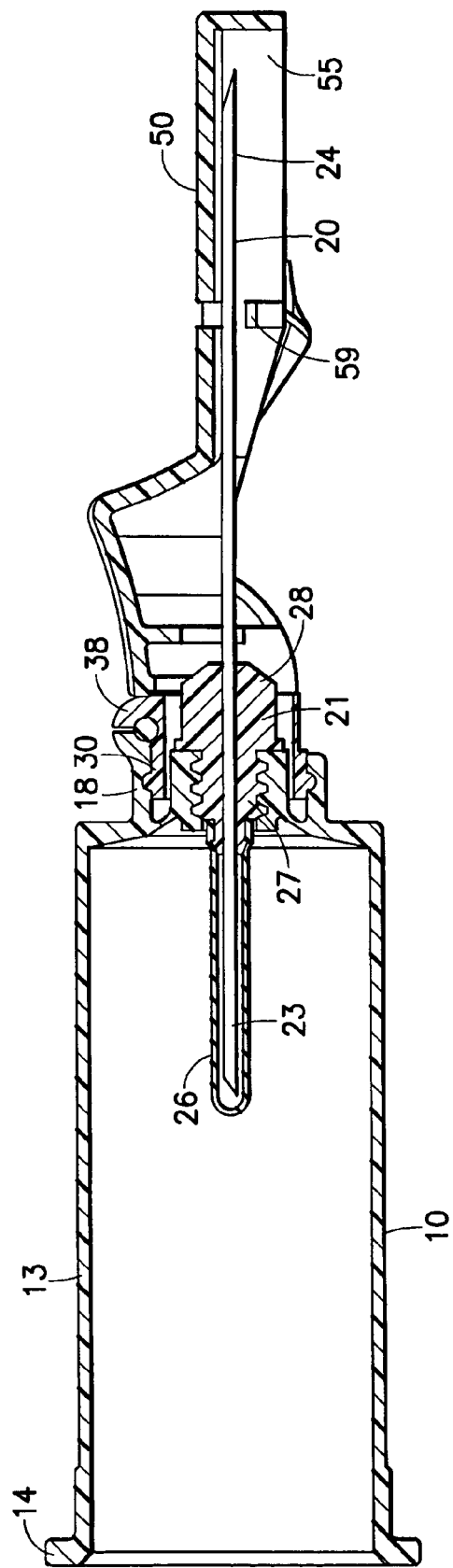
FIG. 10 is a cross-section view of the assembly of the present invention connected to a needle assembly and hub shown in a shielding position.

Hanger bar 51 is provided for pivotal engagement with hook member 38 of collar 30. Accordingly, the cooperating surfaces of hanger bar 51 and hook member 38 are designed so as to permit rotational or pivotal movement of safety shield 50 with respect to collar 30. Such engagement between hanger bar 51 and hook member 38 provides for pivotal movement of safety shield 50 between a retracted position as shown in FIGS. 1 and 5, and a shielded position encompassing the intravenous end 24 of needle 20 as shown in FIG. 10. One skilled in the art will understand that the hanger bar/hook member attachment means may be replaced by any acceptable alternative such as a rivet or a single piece collar and safety shield.

Referring to FIGS. 1 and 5, the safety shield 50 includes parallel sidewalls 52 that extend downwardly for surrounding collar 30. Parallel sidewalls 52 include an inner surface where barb dents 59 (shown in FIG. 1) are located. The barb dents 59 cooperate with locking dents 39 on collar 30 to secure the pivot shield in its final locked position.

Referring to FIG. 5, the safety shield 50 includes a rearward end 53, a forward end 54 and a slot or longitudinal opening 55 in the forward end 54 for receiving the intravenous end 24 of needle 20 after use.

In a preferred embodiment, the holder assembly of the present invention is mated with a needle assembly for use in common medical procedures. For example, as shown in FIGS. 3-7, the needle assembly of the present invention may be in the form of a modified double-ended needle assembly for mating with a needle holder capable of accommodating a collection tube for sampling procedures. Needle 20 includes a non-patient end 23, an intravenous end 24 and a passageway 25 extending between the non-patient end and the intravenous end. An elastomeric sleeve 26 covers the non-patient end and rigid sleeve 22 covers the intravenous end. Rigid sleeve 22 acts as a packaging cover during assembly prior to use.

Figure 6:
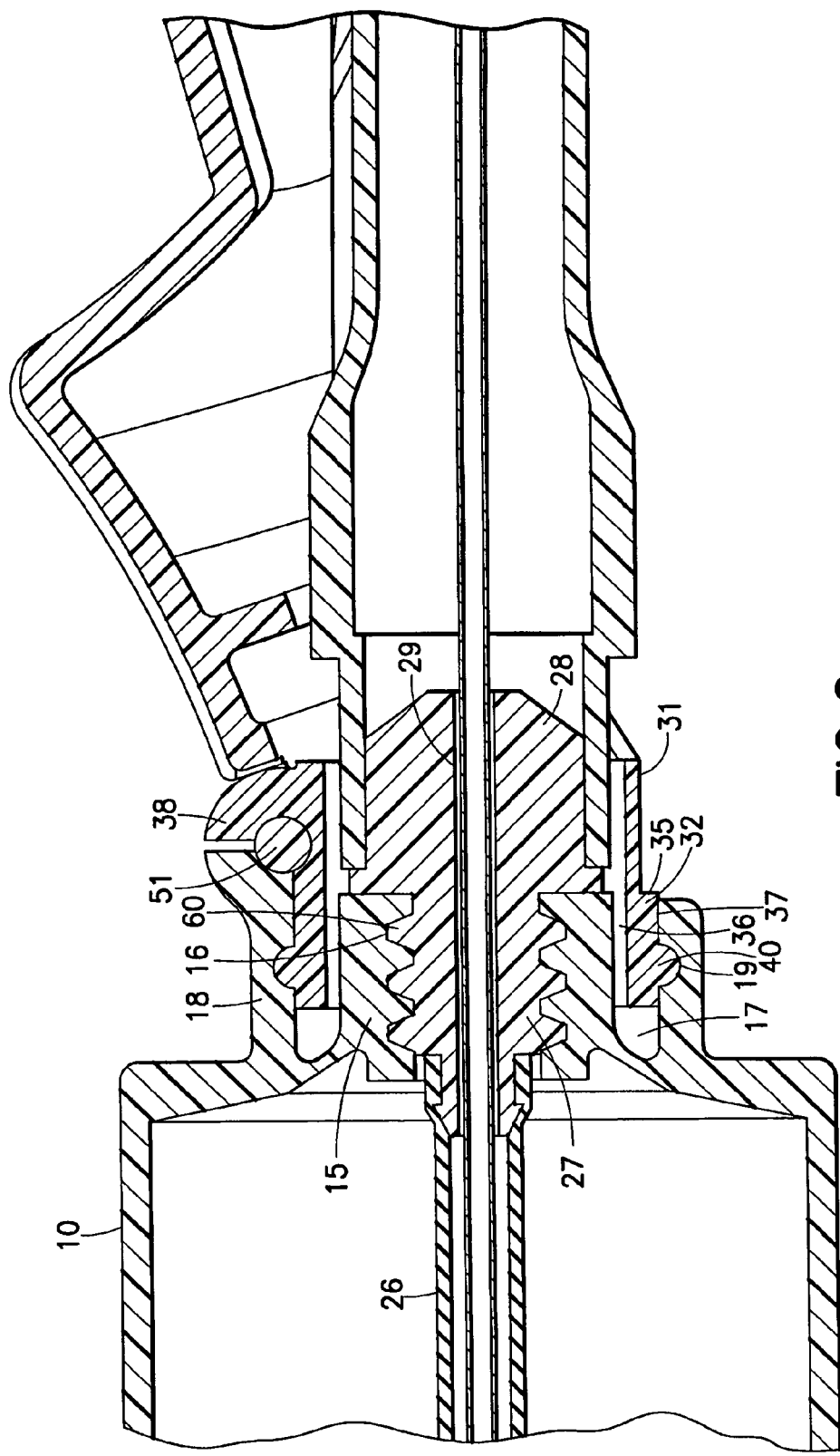
FIG. 6 is an enlarged view of a portion of FIG. 5 showing the engagement between the collar and the annular skirt of the holder housing.

As shown in FIGS. 5 and 6, hub 21 includes a threaded end 27, non-threaded end 28 and passageway 29 extending between the threaded end 27 and non-threaded end 28. Non-patient end 23 of needle 20 extends from threaded hub end 27 and intravenous end 24 of needle 20 extends from non-threaded hub end 28. Preferably, threaded hub end 27 comprises threads 60 for mounting the hub on holder housing 10.

As noted, in the preferred embodiment, forward end 12 of holder housing 10 includes needle receiving port 15 which may be formed with internal threads 16. Threads 16 are engageable with threads 60 of threaded hub end 27 of hub 21. It is understood by those skilled in the art that holder housing 10 and hub 21 may be mated or mounted together in many known ways, such as through ribs or adhesive. The holder housing 10 including shield assembly 50 attached thereto and the needle assembly including needle 20 and hub 21 may be supplied separately, may be supplied as a preassembled single unit, or may be permanently attached.

Alternatively, the needle assembly including hub 21 may be attached directly to collar 30, such as through structure provided within collar 30, for example a threaded engagement between threads 60 and a set of threads (not shown) provided within collar 30, such as on the inner sidewall 33. In such an arrangement, the holder housing need not have any structure for attachment of the needle assembly. The collar 30 can be attached directly to the forward end 12 of holder housing 10, with annular skirt 18 extending as the outer perimeter of forward end 12 of holder housing 10 and with collar 30 attached within annular skirt 18. In this manner, the needle assembly including needle 20 can be attached to the inner sidewall 33 of collar 30 with the non-patient end of needle 20 extending through the forward end 12 of holder housing 10.

Alternatively, needle 20 can be attached directly to collar 30 or directly to holder housing 10 at needle receiving port 15, without the need for separate structure such as hub 21.

FIG. 7 illustrates the order of attachment of the needle assembly, including hub 20, collar 30 and holder housing 10. FIG. 6 provides an enlarged view of the attachment of collar 30 to the holder housing 10 by means of the placement of rearward collar section 32 of collar 30, and the annular protrusion or protuberance 40 on outer sidewall 37 thereof, within annular groove 19 of the holder housing 10. Protrusion 40 mates with groove 19. In the attached position, annular skirt 18 of holder housing 10 encompasses at least a portion of the rearward collar section 32 of the collar 30. The collar 30 is connected to holder housing 10 by means of the frictional interaction between protrusion 40 and groove 19. In particular embodiments, the collar 30 may be freely rotatable with respect to the holder housing 10 about an axis of the holder housing 10 which corresponds to that of needle 20. The ease of such rotation of collar 30, and corresponding rotation of shield 50, is based on the friction between the groove 19 and protrusion 40. As such, it may be possible to adjust the ease of rotation of collar 30 by appropriately molding the geometry of protrusion 40 and groove 19 to have more or less friction therebetween. In embodiments where rotation of collar 30 with respect to holder housing 10 is desired, the friction level should be sufficient to maintain the connection between the holder housing 10 and the collar 30 in the absence of separating force. In a preferred embodiment, the friction is such that the collar 30 is not freely rotatable within the annular skirt 18 of the housing holder 10, but that some force is required to cause rotation.

It should be understood that annular skirt 18 surrounds the exterior of the rearward collar section 32 of collar 30, thus helping to prevent the disconnection of collar 30 from housing holder 10 through accidental force. In a preferred embodiment, annular skirt 18 of holder housing 10 extends from holder housing 10 to a point where it abuts or encloses the open end of hook member 38 of collar 30 as shown in FIG. 6, thus providing additional protection against the accidental dislocation of safety shield 50.

In such an embodiment, it is also contemplated that the structure extending from annular skirt 18 of holder housing 10 interacts with the structure of hook member 38 to provide structure for a rotational or pivoting axis for safety shield 50. In particular, as discussed above, hangar bar 51 is pivotably engaged with hook member 38 to provide a pivot hinge for the pivoting of safety shield 50. When annular skirt 18 of holder housing 10 extends to abut or enclose the open end of hook member 38, the interrelation therebetween provides support structure to maintain hangar bar 51 therein, and provides a bearing surface with the extension of annular skirt 18 acting as a rearward bearing surface and the hook member 38 acting as a forward bearing surface. In this manner, hangar bar 51 thereby forms a journal for rotational movement within the bearing surfaces, thereby establishing a rotational axis for hangar bar 51 and safety shield 50.

Also, the extension of annular skirt 18 allows for sufficient support structure for hangar bar 51, while preventing disengagement of hangar bar 51 and removal of shield 50 from the assembly. Hook member 38 therefore creates only a portion of the support structure for hangar bar 51, with a reduced inner circumference of hook member 28 acting as the forward bearing surface for engagement with hangar bar 51. This feature also facilitates assembly, in that the opening on the rearward end of hook member 38 is wider and may be of the same inner diameter as the outer diameter of hangar bar 51, and therefore requires less force to engage the hook member 38 over hangar bar 51. Desirably, the rearward bearing surface of the extension of annular skirt 18 and the forward bearing surface of the hook member 38 each represent at least about 30% of the arc of the bearing surface measured with respect to the journal established by hangar bar 51. In such an embodiment, the collar 30 is desirably restricted from rotation with respect to the holder housing 10 after assembly.

Figure 11:
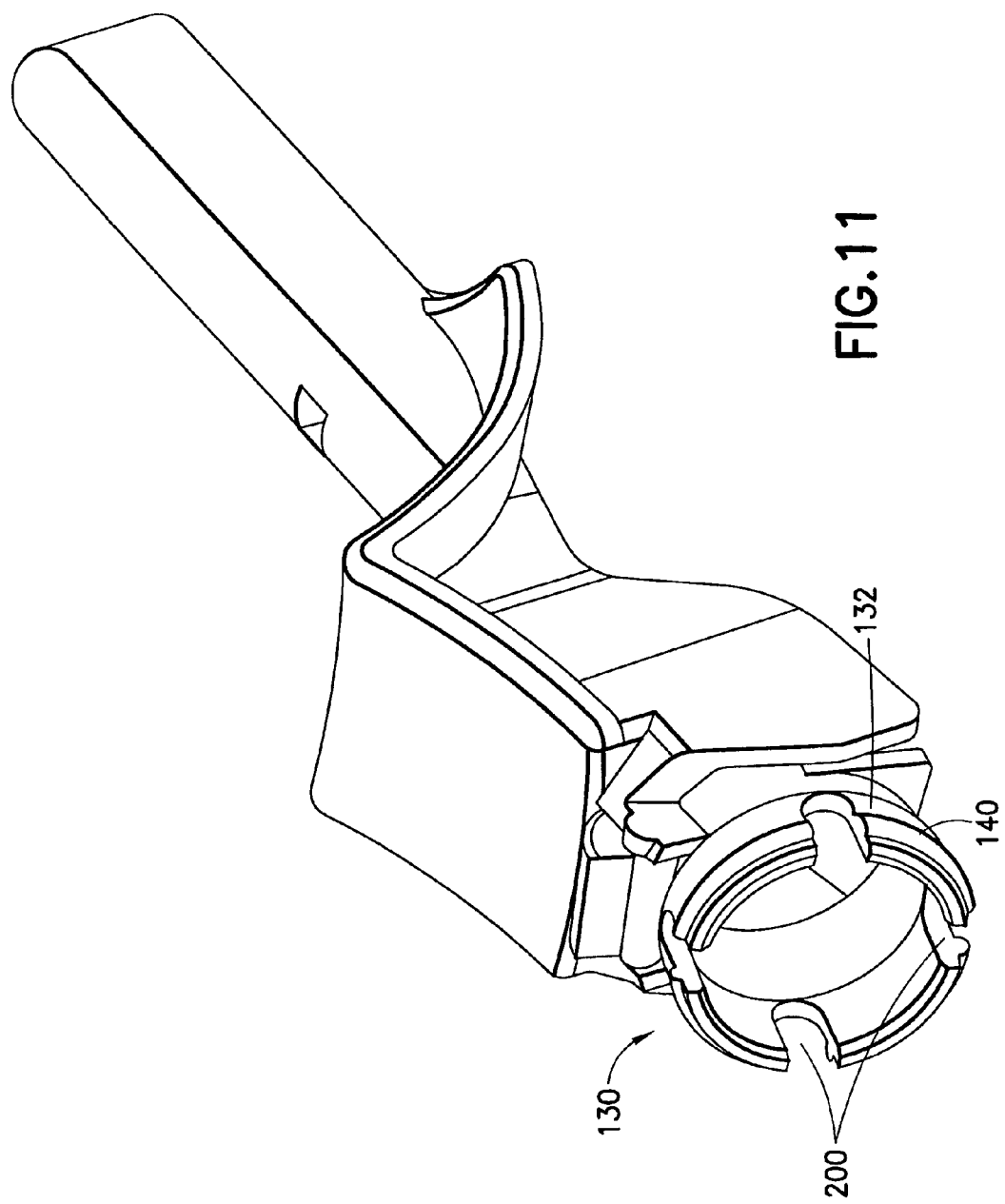
FIG. 11 is a perspective view of an additional embodiment of the collar of the assembly.

FIG. 11 is a further embodiment of the invention which includes an alternate collar design. Rearward collar section 132 and annular protrusion 140 of collar 130, are shown which are of a slitted design, including a plurality of slits 200. As in the preferred embodiment, protrusion 140 mates with groove 19 in recess 17 to mate the holder housing 10 with collar 130. The slitted design allows for additional flex in rearward collar section 132 of collar 130, and may enable the insertion thereof into recess 17 of holder housing 10 with less force. One skilled in the art will know that one or more slits can be utilized to achieve the desired flex. The slits may also be of varying width.

Figure 12:
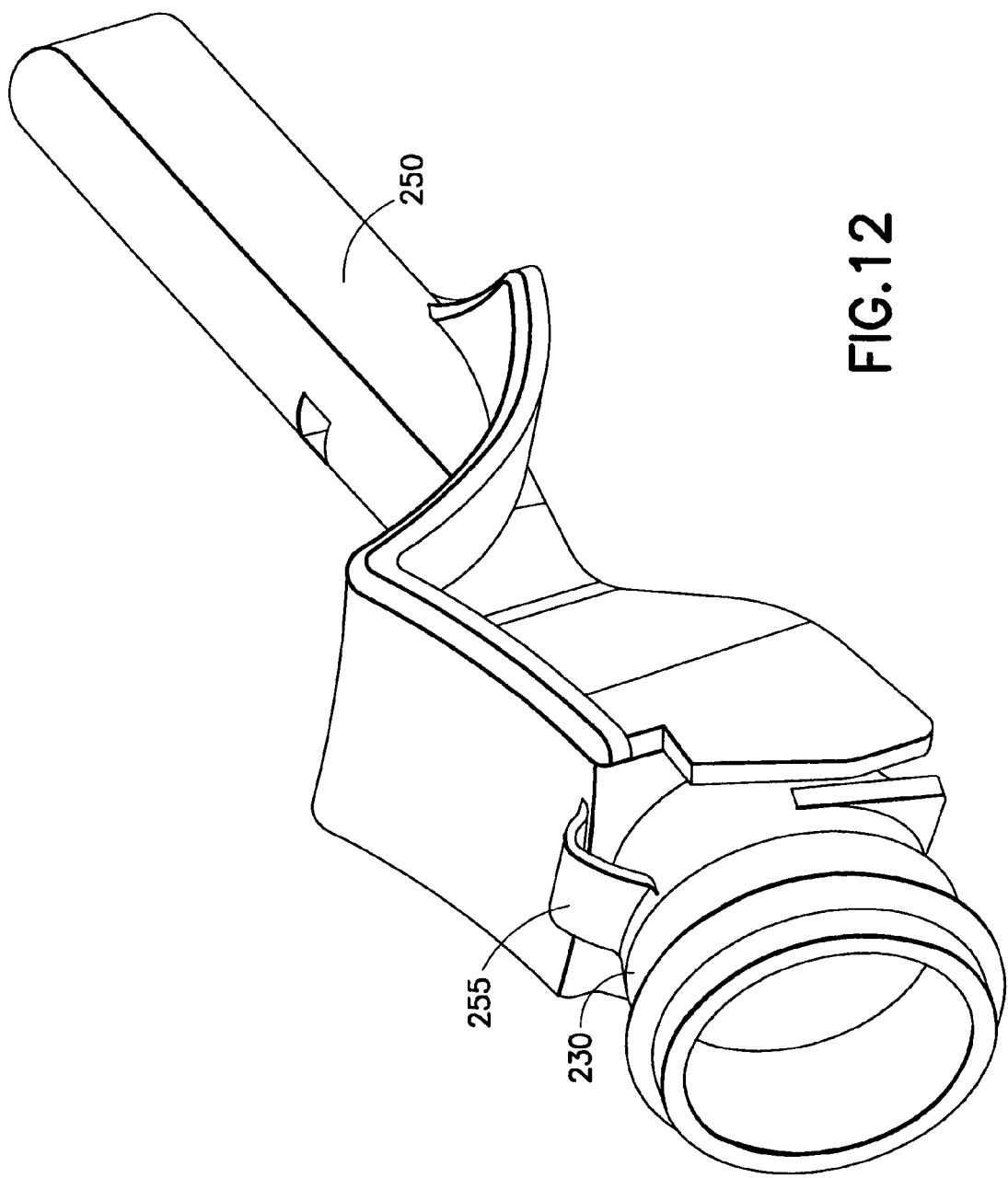
FIG. 12 is a perspective view of the collar and shield in yet a further embodiment of the invention.

FIG. 12 depicts a collar and shield arrangement in a further embodiment of the invention. As shown in the embodiment of FIG. 12, pivotable engagement between shield 250 and collar 230 may be provided through a living hinge, such as hinge strap 255. Hinge strap 255 interconnects shield 250 and collar 230, and may be integrally formed with one or both of shield 250 and collar 230. In the embodiment of FIG. 12, collar 230 is provided for connection with a holder housing, such as an interfitting connection within a recess of a skirt established through a protrusion and groove arrangement, as described above in the main embodiment. As such, collar 230 may be freely rotatable with respect to the holder housing within the recess provided by the skirt, thereby permitting shield 250 to be rotated abut an axis of the holder housing out of the field of sight of the use. With the shield 250 and collar 230 inconnected through hinge strap 255, shield 250 is adapted to pivot with respect to collar 230, to encompass and protectively shield a needle extending therethrough, as in the previously described embodiment.

As used throughout this specification, the word "annular" is meant to include all ring-like shapes, including but not limited to circles, squares, ovals, irregular circumferences and all multi-sided rings having three or more sides. One skilled in the art will likewise understand that the groove and protrusion need not be contiguous. Gaps are acceptable if they do not interfere with the holder housing/collar attachment or the frictional rotation of the collar within the recess of the holder housing.

The needle holder assembly of the present invention may be assembled as described above. Specifically, with reference to FIGS. 6 and 7, safety shield 50 may be attached to hook member 38 of collar 30 by means of hanger bar 51. Collar 30 may then be attached to holder housing 10 by inserting rearward collar section 32 of collar 30 into recess 17 of holder housing 10, so that annular protrusion 40 engages groove 19. Collar 30 thus becomes rotatable within annular skirt 18. The needle assembly may then be attached to the holder assembly by threading hub 21 into holder housing 10. Threads 60 of threaded hub end 27 of hub 21 are threaded into threads 16 of needle receiving port 15 of the holder housing 10.

In use, the safety shield 50 is pivoted back by the user towards the holder housing 10. Due to the frictional attachment of the collar 30 to the holder housing 10 by means of the engagement of the rearward collar section 32 and the protrusion 40 within recess 17 and groove 19, the attached safety shield 50 may be rotated with collar 30 about the longitudinal axis of the holder housing 10 to a desired position. The collar 30 is retained within annular skirt 18 of holder housing 10, thus preventing the accidental disconnection of the collar 30 and connected safety shield 50.

In embodiments in which the needle assembly is provided as a separate assembly for attachment, hub 21 can then be attached to the forward end 12 of holder housing 10, such as by threading within needle receiving port 15. Alternatively, such as needle assembly can be pre-assembled directly with holder housing 10 or within collar 30, as noted above.

The rigid sleeve 22 can then be removed from the intravenous end 24 of the needle 20. Then, a venipuncture is conducted whereby the intravenous end 24 of the needle 20 is inserted into a vein of a patient and an evacuated tube having a closure is inserted into the holder housing 10. When the venipuncture is complete, the user pivots the safety shield 50 from the open position towards the intravenous end 24 of the needle 20 to a final, non-retractable locked position as shown in FIG. 10, whereby the needle is trapped in the longitudinal opening 55 within the forward end 54 of safety shield 50 and barb dents 59 of the safety shield 50 are held by locking dents 39 of collar 30. As the safety shield 50 is pivoted the barb dents deflect over and are held by the locking dents 39. Additionally or instead of the locking engagement provided through such barb dents 59 and locking dents 39, an internal cannula lock 59 may be provided within shield 50, for locking by engaging with needle 20 to maintain shield 50 in a locked position encompassing needle 20. The needle 20 is contained within the safety shield 50 as the pivot shield is pivoted into the closed position.

The safety shield, collar and holder housing of the holder assembly of the present invention are comprised of moldable parts which can be mass produced from a variety of materials including, for example, polyethylene, polyvinyl chloride, polystyrene or polyethylene and the like. Materials will be selected which will provide the proper covering and support for the structure of the invention in its use, but which will provide also a degree of resiliency for the purpose of providing the cooperative movement relative to the holder housing, safety shield and the collar of the assembly.

While the present invention has been described in terms of specific embodiments for use in connection with a blood collection system, it is further contemplated that the assembly and the components thereof can be used with other medical procedures known in the art.

The invention claimed is:

1. A holder assembly comprising:
   a holder housing adapted to receive a sample collection tube within a rearward end, a forward end of the holder housing including;
      a needle receiving port for receiving a needle cannula therein and
      an annular skirt extending about the needle receiving port; and
   a safety shield pivotably attached to a collar, said collar having an opening therethrough for receiving a needle cannula therethrough, the collar being received between the annular skirt and the needle receiving port of the holder housing such that the safety shield is capable of being pivoted over at least a portion of a needle received within the needle receiving port of the holder housing, wherein the safety shield and the collar are axially rotatable with respect to the holder housing about an axis of the holder housing, such that the safety shield and the collar can be radially rotated to a desired position around a needle received within the needle receiving port around the axis of the holder housing without axial movement of the collar along the axis.

2. The holder assembly of claim 1, wherein the collar is annular.

3. The holder assembly of claim 1, wherein the shield comprises a rearward end, a forward end, a longitudinal opening in the forward end for receiving a needle, and a hanger bar on the rearward end adapted to connect the safety shield to the collar.

4. The holder assembly of claim 3, wherein the collar comprises a hook arm, the hook arm engages the hanger bar for connecting the safety shield to the collar whereby there is an interface fit between the hanger bar and the hook arm.

5. The holder assembly of claim 1, wherein an outer surface of the collar includes a protrusion and an inner surface of the annular skirt includes a groove, the groove on the annular skirt adapted to receive the protrusion on the annular collar, thereby providing an interface fit when the collar is received between the annular skirt and the needle receiving port of the holder housing.

6. The holder assembly of claim 5, wherein the protrusion is annular and extends around the outer surface of the collar and the groove is annular and extends around the inner surface of the annular skirt.

7. The holder assembly of claim 4, wherein the annular skirt on the holder housing substantially encloses an open end of the hook arm, thereby preventing the interface fit between the hanger bar and the hook arm from releasing when the collar is received between the annular skirt and the needle receiving port of the holder housing.

8. The holder assembly of claim 1, wherein the collar has one or more slits defined in a rearward annular collar section thereof.

9. The holder assembly of claim 1, wherein the shield and the collar are integral and attached through a living hinge.

* * * * *